United States Patent
Legrand

(10) Patent No.: US 7,628,058 B2
(45) Date of Patent: Dec. 8, 2009

(54) DEVICE AND METHOD FOR THERMODYNAMIC MEASUREMENTS ON PETROLEUM FLUIDS

(75) Inventor: Stéphane Legrand, Paris (FR)

(73) Assignee: Vinci Technologies, Nanterre (FR)

( * ) Notice: Subject to any disclaimer, the term of this patent is extended or adjusted under 35 U.S.C. 154(b) by 235 days.

(21) Appl. No.: 11/682,416

(22) Filed: Mar. 6, 2007

(65) Prior Publication Data
US 2008/0016944 A1   Jan. 24, 2008

(30) Foreign Application Priority Data
Dec. 7, 2006   (FR) .................................. 06 11561

(51) Int. Cl.
*G01N 25/00*   (2006.01)
(52) U.S. Cl. ..................................... 73/64.55
(58) Field of Classification Search ................. 73/64.55
See application file for complete search history.

(56) References Cited
FOREIGN PATENT DOCUMENTS
FR         2856797         12/2004

*Primary Examiner*—Hezron Williams
*Assistant Examiner*—Rodney T Frank
(74) *Attorney, Agent, or Firm*—Antonelli, Terry, Stout & Kraus, LLP.

(57) ABSTRACT

Device for measuring thermodynamic characteristics of a fluid sample, comprising in combination: a high-pressure cell (6) equipped with a motorized piston, a drying oven surrounding the cell and intended to vary the cell temperature, motorization means arranged outside the drying oven, means for stirring the fluid placed within the cell, a frame supporting said oven and means (1) for tilting said frame so as to tip the cell up. The cell comprises:—a specific head for measurements on condensate gas wherein a chamber (42) of elongate shape along the axis of the cell is intended to collect the liquids, and—means (44) for visualizing the position of the liquid/gas interface.

8 Claims, 2 Drawing Sheets

DEVICE AND METHOD FOR THERMODYNAMIC MEASUREMENTS ON PETROLEUM FLUIDS

FIELD OF THE INVENTION

The present invention relates to the field of studies referred to as PVT studies of petroleum reservoir fluids. In particular, the invention relates to a device allowing optimized measurements on complex fluids.

BACKGROUND OF THE INVENTION

It is necessary to know the behaviour of the fluids contained in a reservoir rock to be able to estimate the recoverable oil and gas amounts, and to determine the separation conditions allowing a maximum proportion of liquid products to be obtained. The behaviour of hydrocarbon mixtures can be studied in the laboratory in steel cells wherein it is possible to vary the volume provided for the fluid by mercury intrusion or retraction by means of a positive-displacement mercury pump connected thereto. Other pressurization and volume variation mechanisms are used, for example by means of a motorized piston interior to the cell. The temperature of the cell is controlled and portholes made of a transparent material allow to observe the first fog formation (dew point) and the condensed volumes. The study can be performed with a constant or a variable mass.

The cells that are currently known involve drawbacks and limitations, notably as regards the low volume of fluid tested because of the technically possible small cell size, the low-performance visualization means, the measuring means linked with detection of the gas/liquid interface position, etc.

Document FR-2,856,797 describes a measuring device and method comprising a cell tilting system for measurements on condensate gases or liquids. However, the interface visualization system is not optimal, notably as regards the study of condensate gases.

SUMMARY OF THE INVENTION

The present invention thus relates to a device for measuring thermodynamic characteristics of a fluid sample, comprising in combination: a high-pressure cell equipped with a motorized piston, a drying oven surrounding said cell and intended to vary the temperature of said cell, motorization means arranged outside the drying oven, means for stirring the fluid placed within the cell, a frame supporting said oven and means for tilting said frame so as to tip the cell up. The cell comprises: a specific head for measurements on condensate gas wherein a chamber of elongate shape along the axis of the cell is intended to collect the liquids, and means for visualizing the position of the liquid/gas interface.

The dimensions of the elongate chamber can be such that the section thereof is about 2 cm$^2$ and the length thereof ranges between 10 and 15 cm.

The cell can comprise another specific head for measurements on liquid hydrocarbons.

The means for visualizing the position of the liquid/gas interface can comprise a digital camera connected to a liquid/gas interface recognition software.

The software can automatically control the movement of the camera according to the movement of the interface.

The invention also relates to a method for measuring thermodynamic characteristics of a fluid sample in the device according to the invention, wherein the cell is tilted so as to switch from measurements on a hydrocarbon oil sample to measurements on a condensate gas sample, after mounting the head specific to gas or to liquids.

The condensation or evaporation volumes and flow rates can be measured from digital camera movement data.

BRIEF DESCRIPTION OF THE FIGURES

Other features and advantages of the present invention will be clear from reading the description hereafter of a non-limitative embodiment illustrated by the accompanying figures wherein.

DETAILED DESCRIPTION

Figure 1:
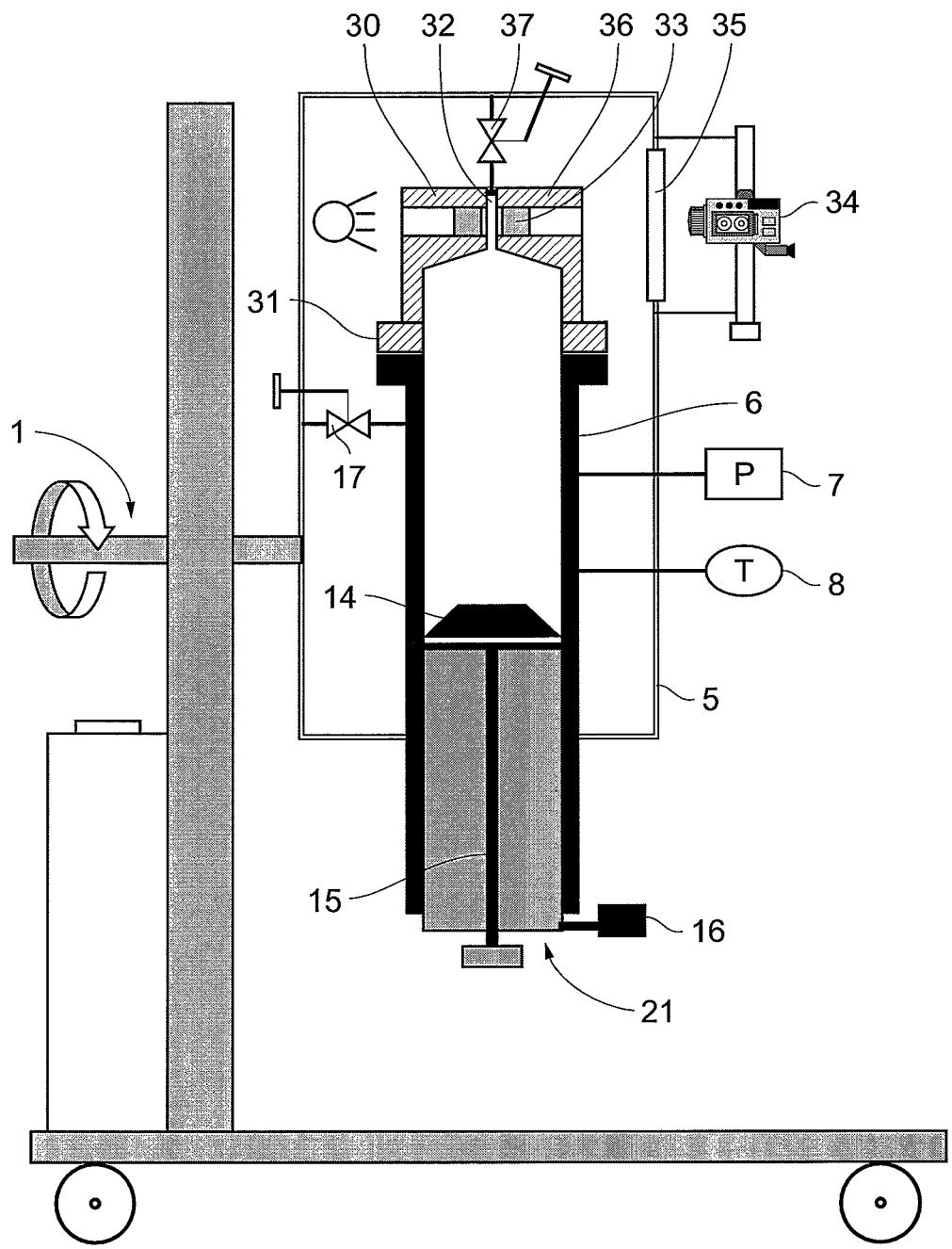
FIG. 1 diagrammatically shows the device equipped with the "oil head" configuration, FIG. 2 diagrammatically shows the device equipped with the "condensate gas head" configuration.

FIG. 1 describes a device comprising a cylindrical cell 6 made of stainless steel that is heated or cooled by a climatic oven 5 wherein this cell is contained. The cell is provided with a motorized piston 15 allowing pressurization of the petroleum fluid fed into inner space 20 of the cell through feed valve 17. The piston moves within the cell by means of motorization means 16, for example an electric or hydraulic jack system, whose motion can be controlled with precision. The motorization means comprise a position coder, which allows to measure the movement and to know the position of the piston, therefore the volume of fluid in the cell.

It can be noted that the mechanical piston motorization means are outside climatic oven 5 and arranged in a simple housing 21, which allows the volume of the climatic cell to be reduced so as to decrease the thermal inertia and the energy consumption thereof.

A pressure detector 7 and a temperature probe 8 respectively measure the pressure and the temperature of the fluid in the cell.

The fluid is mixed in the cell by stirring means comprising a rotor 14 driven by a rotating magnetic field. This substantially truncated-cone-shaped rotor has the particular feature of creating, in the inner space of the cell, a minimum dead volume. Grooves, for example of hollow spiral shape, are machined in the surface of the truncated cone. When the rotor is rotating, a vortex forms in the fluid, which allows efficient stirring to be obtained.

Cell 6 is closed in the upper part thereof by a head 30 suited for measurements on essentially liquid oils. This head, for example assembled by a conventional flange system 31, comprises a small-volume chamber 32 allowing to visualize the appearance of gas after test procedures. Visualization is achieved by monitoring the appearance of an oil/gas interface by means of a porthole 33 and of a camera 34 positioned before a window 35 in the housing of drying oven 5. A line 36 controlled by a valve 37 allows to bleed the visualization chamber if need be.

In this configuration, the tests are generally carried out with the cell substantially vertical and head 30 at the top.

The assembly made up of the drying oven and of the piston motorization is mounted on a frame equipped with a tilting and tipping system 1, for example a flywheel and a reducer mounted on a shaft of the frame. This system allows the operating mode to be changed. In normal position, the configuration of the device allows a PVT study to be carried out on an oil sample. The liquid is in the bottom of the cell in the immediate vicinity of the space stirred by propeller 14 whereas the gas, lighter than the liquid, is in an upper position and can be discharged through line 36 if one wishes to. The liquid/gas interface can be observed through porthole 33 while the gas is discharged through outlet valve 37. The collecting chamber is small and it has no other function than to allow visualization of the appearance of gas bubbles. In tilted position, the device is used to test a condensate gas sample.

Figure 2:
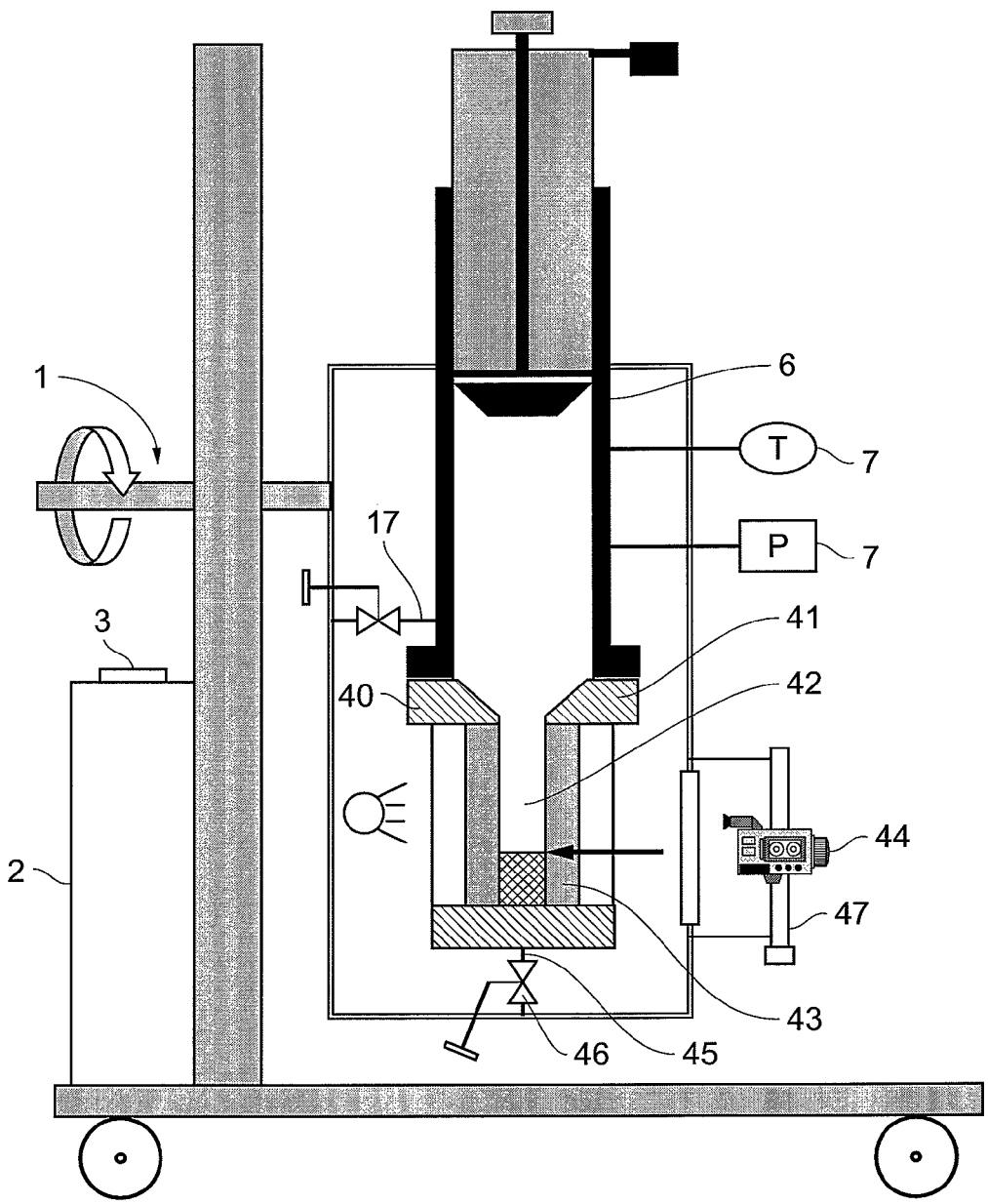

FIG. 2 shows this position wherein head 40 suited for condensate gases is at the bottom of cell 6. The condensate gas head comprises a flange joint type system 41 that corresponds to the flange of cell 6. The head comprises a chamber 42 for collecting the condensates obtained while measuring. This chamber can have the approximate dimensions of a 1-cm diameter and 20 to 30-cm long cylinder, or have a rectangular section of 2 $cm^2$ and a length of 10 to 15 cm, thus allowing to obtain a volume ranging between approximately 20 and 30 $cm^3$. The elongate shape is so selected that the motion of the liquid/gas interface in this chamber can be observed with precision for a low liquid volume variation. Thus, the measurement of the condensate volume variation will be accurate. What is referred to as elongate means that the ratio of the length of the chamber to the average width of the cross-section thereof ranges between 4 and 20, for a chamber volume ranging between 10 and 30 $cm^3$. Part of the wall of this chamber is made of a transparent material 43 so as to allow visualization of the liquid/gas interface.

A digital camera 44 placed opposite a window provided in the wall of the drying oven is therefore used. A line 45 controlled by a valve 46 allows to bleed the cell and notably to expel the condensates in the position according to FIG. 2. The digital camera is connected to a computer that comprises an interface line recognition software which automatically controls the movement of the camera on a supporting rail 47 so as to monitor the rise or the fall of the liquid/gas interface line. These measurements directly linked with the formation of condensates are very accurate, which improves volume and flow rate calculations.

An electric box 2 includes an automaton that manages the input/output parameters of the various components and detectors, as well as the motorization speed variation controls. An on-screen keyboard 3 allows the device to be locally controlled by the user.

The device according to the invention is dedicated to the analysis of the thermodynamic behaviour of petroleum fluids that may exist in form of condensate gas or oil. This analysis is carried out under the pressure and temperature conditions that prevail in the reservoir where the petroleum fluid studied was taken. This is the reason why the HP/HT cell according to the invention, referred to as "PVT cell", is designed to withstand a pressure of the order of 1000 bar and a temperature of approximately 200° C. The goal of any PVT experiment is to measure the volumes of the liquid and gas phases of the fluid according to the pressure and the temperature. The fluid is therefore fed into the PVT cell through valve 17, heated to the desired temperature through thermal control of drying oven 5, then pressurized by controlled displacement of piston 15. The operator can then vary the set temperature and pressure values while measuring the gas and liquid volumes of the petroleum fluid, under these pressure and temperature conditions.

Thermodynamic equilibrium is reached more quickly when the mixture is properly stirred, which is the case with the stirring means according to the invention that leave no dead volume.

The modular design with two heads, one intended for oils, the other for condensate gases, can provide accurate and reproducible PVT measurements from a large sample volume insofar as the design of the device allows to reach cell volumes up to 1000 $cm^3$.

The invention claimed is:

1. A device for measuring thermodynamic characteristics of a fluid sample, comprising in combination:
   a high-pressure cell equipped with a motorized piston;
   a drying oven surrounding said cell and intended to vary the temperature of said cell;
   motorization means arranged outside the drying oven;
   means for stirring the fluid placed within the cell;
   a frame supporting said oven and means for tilting said frame so as to tip the cell up, characterized in that said cell comprises: a first specific head for measurements on condensate gas comprising a chamber of elongate shape along the axis of the cell intended to collect the liquids; and
   means for visualizing the position of the liquid/gas interface.

2. A device as claimed in claim 1, wherein the dimensions of said elongate chamber are such that the section thereof is about 2 $cm^2$ and the length thereof ranges between 10 and 15 cm.

3. A device as claimed in claim 1, wherein the cell comprises a second specific head for measurements on liquid hydrocarbons, which is interchangeable with the first specific head for measurements on condensate gas.

4. A device as claimed in claim 1, wherein said means for visualizing the position of the liquid/gas interface comprise a digital camera connected to a liquid/gas interface recognition software.

5. A device as claimed in claim 4, wherein said software automatically controls the movement of the camera according to the movement of the interface.

6. A method for measuring thermodynamic characteristics of a fluid sample in the device as claimed in claim 3, wherein the cell is tilted so as to switch from measurements on a hydrocarbon oil sample to measurements on a condensate gas sample, after mounting the first or the second head specific to gas or to liquids.

7. A method as claimed in claim 6, wherein the condensation or evaporation volumes and flow rates are measured from digital camera movement data.

8. A device as claimed in claim 1, wherein a section of said chamber is smaller than a section of said cell.

* * * * *